United States Patent [19]
Giordano

[11] Patent Number: 5,843,348
[45] Date of Patent: Dec. 1, 1998

[54] METHOD FOR FABRICATING ODONTOFORMS AND DENTAL RESTORATIONS HAVING INFUSED CERAMIC NETWORK

[75] Inventor: Russell A. Giordano, Sudbury, Mass.

[73] Assignee: Trustees of Boston University, Boston, Mass.

[21] Appl. No.: 854,805

[22] Filed: May 12, 1997

Related U.S. Application Data

[63] Continuation of Ser. No. 307,455, Sep. 19, 1994, abandoned.

[51] Int. Cl.$^6$ ..................................................... A61C 13/08
[52] U.S. Cl. ........................... 264/19; 264/628; 264/643; 264/651; 427/2.26
[58] Field of Search .............................. 264/628, 16, 19, 264/643, 651; 427/2.26

[56] References Cited

U.S. PATENT DOCUMENTS

| | | | |
|---|---|---|---|
| 3,250,833 | 5/1966 | Wagner | 264/628 |
| 3,423,828 | 1/1969 | Halpern . | |
| 3,713,860 | 1/1973 | Auskern | 117/8.5 |
| 4,772,436 | 9/1988 | Tyszblat . | |
| 4,777,153 | 10/1988 | Sonoparlak et al. | 501/82 |
| 5,164,233 | 11/1992 | Sonoparlak et al. | 427/399 |
| 5,221,558 | 6/1993 | Sonoparlak et al. | 427/376.1 |
| 5,427,722 | 6/1995 | Fouts et al. | 264/87 |

FOREIGN PATENT DOCUMENTS

| | | |
|---|---|---|
| 0241120 | 10/1987 | European Pat. Off. . |
| 0241384 | 10/1987 | European Pat. Off. . |
| 0393525 | 10/1990 | European Pat. Off. . |
| 0241384 | 10/1987 | France . |
| 63-041519 | 2/1988 | Japan . |
| 63-252981 | 10/1988 | Japan . |

OTHER PUBLICATIONS

S. Sonuparlak, *Tailoring the Microstructure of Ceramics and Ceramic Matrix Composites through Processing 37*, Composites Science and Technology 299–312 (1990).

A.S. Fareed, et al., *Mechanical Properties of 2–D Nicolon™ Fiber–Reinforced LANXIDE™ Aluminum Oxide and Aluminum Nitride Matrix Composites*, Ceram. Eng. Sci. Pro. 782–794 (1990).

*Primary Examiner*—Christopher A. Fiorilla
*Attorney, Agent, or Firm*—Samuels, Gauthier, Stevens & Reppert

[57] ABSTRACT

A process for producing a ceramic network material from a ceramic suspension includes casting a suspension in a tooth-shaped mold. The suspension includes dispersed alumina particles in a medium containing deionized water with a pH in a range of about 4 to 5 and a concentration of polyvinyl alcohol in a range of about 0.5 to 1% by weight. The process includes the steps of slip casting the suspension in a plaster tooth mold and drying the molded suspension to draw the water from the suspension. The dried suspension then is fired in a furnace at a temperature in a range of about 1000 to 1400° C. to form a ceramic network. After the dried suspension has been fired and excess water and polyvinyl alcohol has been removed from the suspension, lanthanum aluminosilicate glass is infused to a coronal portion of the ceramic network to form a glass layer with a thickness in a range of about 1 to 2 mm within the ceramic network. A monomer, such as a monomer solution, then is infused to at least the portion of the ceramic network within the glass layer. Alternatively, the ceramic network may be infused with a metal alloy to form a layer on the coronal portion or with one or more monomers.

38 Claims, 3 Drawing Sheets

METHOD FOR FABRICATING ODONTOFORMS AND DENTAL RESTORATIONS HAVING INFUSED CERAMIC NETWORK

This application is a continuation of appliction Ser. No. 08/307,455 filed Sep. 19, 1994, entitled "INFUSED CERAMIC NETOWRK FOR FABRICATING ODONTOFORMS AND DENTAL RESTORATIONS", now abandoned.

BACKGROUND OF THE INVENTION

1. Field of the Invention

The invention relates to ceramic network materials used to produce odontoforms which replicate the physical and mechanical properties of natural teeth. Further, this invention relates to fabricating dental restorations and, in particular, to an interpenetrating network material which may be used as a restorative material. This restorative material may be used to fabricate restorations, such as inlays, onlays, crowns, and bridges, by centrifugal or pressure casting in mastercast molds or by machining blocks of the restorative material.

2. Description of Related Art

Figure 1:
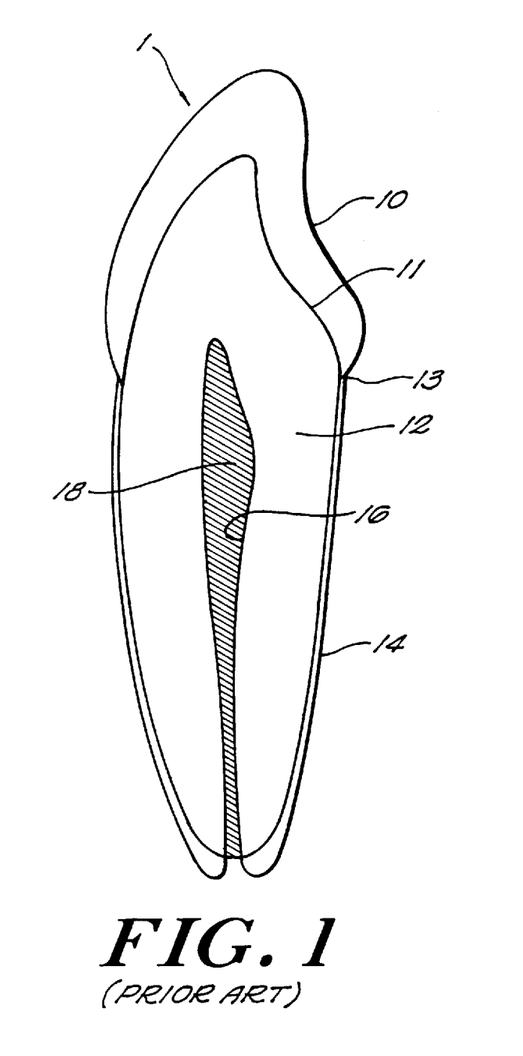
FIG. 1 is a cross-sectional view of a natural tooth.

Referring to FIG. 1, natural tooth enamel 10 is a hard, vitreous substance that covers the outer portions on a tooth crown 1. Mature enamel is highly mineralized, containing about 96 to 98% inorganic substance. Its most abundant mineral component, i.e., about 90%, is hydroxyapatite, which is crystalline.

Hardness is an important enamel property because enamel 10 provides a protective covering for the softer underlying dentin 12. Enamel 10 also serves as a masticatory surface on which food is crushed, ground, and chewed. Specifically, hardness is a measure of the ability of tooth enamel to withstand deformation by indentation or scraping, or the like, and mature enamel demonstrates a Knoop hardness number (KHN, i.e., the ratio of a given load to an area of indentation expressed in Kg/mm$^2$) in a range of about 200 to 500 KHN. Measurement of tooth enamel's microhardness is valuable not only in assessing its plastic properties in relation to masticatory forces, but also as a consideration in the selection of restorative materials.

Generally, the density of enamel 10 decreases from its surface to the dentinoenamel junction 11. Further, the thickness of enamel 10 may vary throughout different regions of the tooth and from one type of tooth to another. For example, over the cusps of molars, enamel may attain an average thickness of about 2.6 mm; over the cusps of premolars, it may be about 2.3 mm; and over the incisor edge of incisors, it may be about 2 mm thick. Enamel 10 may become progressively thinner towards the cervical regions, and its thickness decreases even further towards the cementoenamel junction 13. Enamel coverage usually terminates at cementoenamel junction 13.

Because enamel is semitranslucent, the color of enamel depends in part upon its thickness. For this reason, enamel may assume the various colors of its underlying structures. Thus, when enamel is thicker, and consequently more opaque, it may appear grayish or bluish white reflecting more of its inherent coloration. When enamel is relatively thin, however, it may be yellow-white in appearance, reflecting the underlying generally-yellowish dentin.

Regardless of its thickness or color, enamel is hard in order to function properly as a masticatory surface, yet hardness alone may not be sufficient to enable enamel to withstand the pressure brought to bear on each tooth during mastication. To the contrary, enamel's hardness, as reflected by its brittleness, may represent a structural weakness. In fact, natural enamel is prone to splitting and chipping. For the most part, however, enamel does withstand masticatory pressures, and this may be due in part to the cushioning effect of the underlying dentin. Enamel may possess a relatively high elastic modulus, e.g., about $19 \times 10^6$ PSI, which may suggest that it is extremely brittle, and a relatively low tensile strength, e.g., about 11,000 PSI, which may suggest that it has a rigid structure. Dentin 12, on the other hand, is a highly compressive tissue having compressive strength of about 40,000 PSI and acts as a cushion for overlying enamel 10. Thus, in addition to the properties discussed above, the ability of a tooth to withstand masticatory forces may be related to the physical and mechanical interrelationship between enamel 10 and dentin 12.

As demonstrated by FIG. 1, dentin 12 may constitute the largest single component of tooth structure, extending almost the entire length of the tooth. Dentin 12 is covered by enamel 10 on the crown 1 and by cementum 14 on root 2. The internal surface of dentin 12 forms the walls of a pulp cavity 16 which primarily contains pulpal tissue 18. Further, the walls of pulp cavity 16 may closely conform to the outline of the external surface of the dentin 12.

Dentin and bone in general are natural ceramic-composites. Chemically, dentin 12 is composed of organic and inorganic matter. As noted above, the inorganic matter includes calcium phosphate in the form of hydroxyapatite $(Ca_{10}(PO_4)_6(OH_2))$. The organic matter is primarily collagenous material. Particles of hydroxyapatite, the ceramic, are bonded together by collagenous material, an organic polymer.

The hardness of dentin 12 is less than that of enamel, but generally greater than either cementum or other bone. Further, microhardness values may vary in the different layers (not shown) of dentin 12. The highest microhardness values of intact dentin 12 generally occur in the area about 450 $\mu$m from the dentinoenamel junction 11, with an average KHN of about 70. The lowest microhardness value, e.g., about 20 KHN, may be found in the innermost layer of dentin at distances of about 100 $\mu$m from the pulp. Moreover, with advancing age, the microhardness of dentin 12 tends to increase. A comparison of representative microhardness values of dentin, enamel, and restorative materials is shown in Table I.

TABLE I

| Comparison of Microhardness Values | |
|---|---|
| Materials | KHN |
| Dentin | 65 |
| Enamel | 300 |
| Silicate cement | 70 |
| Gold (pure) | 32 |
| Amalgam | 90 |

Although dentin may be considered a hard structure, it also has elastic properties which may be important for the support of the relatively brittle and non-resilient enamel, as described above. Dentin may have a modulus of elasticity of about $1.67 \times 10^6$ PSI. Moreover, the tensile strength of dentin, e.g., about 6,000 PSI, is less than that of compact bone.

Restorative materials generally are tested on three criteria: sufficient hardness, adequate fit, and acceptable aesthetics, e.g., color match. Of these three, however, aesthetics often are the deciding factor in the choice of restorative materials. Composite resins and ceramics are in widespread use due in part to their ability to match the color of a patient's natural teeth. Composite resins may be composed of a glass in a polymer matrix. This combination, however, may result in rapid wear of the restoration, as the softer polymer is lost, and the glass filler pulls out of the remaining polymer. High wear rates are associated with rapid loss of restorative strength. Restorative ceramics may also be problematic. Despite relatively high hardness, ceramic materials also are generally brittle, such that they may withstand only minimal deformation without failing. Thus, wear in current composite resin materials and catastrophic fracture of ceramic restorations are significant limitations of currently available restorative materials.

Dental students generally learn to restore teeth in the laboratory before working on patients' teeth. Extracted teeth are in limited supply, however, so students often use odontoforms for practice. Further, because of the scarcity of suitable patients for examination purposes, students may be tested for graduation or licensure, in part, on their ability to cut and prepare odontoforms for restorations. Present odontoforms may consist of molded white plastic. Such plastic teeth, however, bear little or no resemblance to natural teeth with respect to mechanical properties, e.g., hardness or elastic modulus, or physical properties, e.g., how the tooth structure feels when being cut with a diamond bur in a dental handpiece. Thus, odontoforms currently used are inadequate to represent and teach the natural tooth structure for purposes of education or examination.

SUMMARY OF THE INVENTION

Thus, a need has arisen for an odontoform which more closely possesses the physical and mechanical properties of natural teeth to adequately prepare students for dental practice on patients and for use in board examinations to qualify such students as dentists. Further, a need has arisen for a restorative material which combines the beneficial restorative qualities of polymers with those of ceramics, and yet avoids disadvantages of polymers.

An embodiment of the invention is a process for producing a ceramic network material from a ceramic suspension. The suspension includes dispersed ceramic particles in a medium containing water and a dispersant. The process includes the steps of casting the suspension in a mold and drying the molded suspension to draw the water from the suspension. The dried suspension then is fired to produce a ceramic network, and a monomer is infused to at least a portion of the ceramic network. Alternatively, a metal, such as a metal alloy, having a melting point at least about 50° C. less than the ceramic or a low fusing temperature glass may be infused to at least a portion of the ceramic network. Suitable glasses have fusing temperatures less than about 900° C., e.g., in a range of about 450°–900° C.

Another embodiment of the invention is a process for producing a ceramic network material from a ceramic suspension by casting said suspension in a tooth-shaped mold. The suspension includes dispersed alumina particles in a medium containing deionized water with a pH in a range of about 4 to 5 and a dispersant, such as a concentration of polyvinyl alcohol in a range of about 0.5 to 2% by weight. The process comprises the steps of casting the suspension in the mold and drying the molded suspension to draw the water from the suspension. The dried suspension then is fired in a furnace at a temperature in a range of about 1000° to 1400° C. to produce a ceramic network. After firing is complete and excess water and polyvinyl alcohol have been removed from the ceramic network, a low fusing temperature glass, such as lanthanum aluminosilicate glass, may be infused to a coronal portion of the fired suspension to form a glass layer within the fired suspension with a thickness in a range of about 1 to 2 mm. A monomer then may be infused to at least a portion of the ceramic network within the glass layer.

Yet another embodiment of the invention is a process for producing a ceramic network material from a ceramic suspension by casting said suspension in a mold to form a block of restorative material. The suspension includes ceramic particles having diameters in a range of about 0.1 to 10 $\mu$m dispersed in a medium containing deionized water with a pH selected from the group of ranges consisting of about 2 to 6 and about 8 to 11 and a dispersant, such as a concentration of polyvinyl alcohol in a range of about 0.1 to 2% by weight. The process comprises the steps of casting the suspension in the mold and drying the molded suspension to draw the water from the suspension. The dried suspension then is fired in a furnace at a temperature in a range of about 600° to 1400° C. to produce a ceramic network. For example, if the dispersed ceramic particles are metal oxides, the suspension may be fired in a furnace at a temperature in a range of about 1000° to 1400° C. However, if the dispersed ceramic particles are feldspathic glasses, the suspension instead may be fired in the furnace at a temperature in a range of about 600° to 1200° C. A monomer then may be infused to at least a portion of the ceramic network. The infused monomer may be a solution including one or more monomers. Additionally, a precipitant, such as acetone or citric acid, may be added to the suspension to remove excess water and dispersant from the suspension before or after the step of casting the suspension in the mold.

A restorative material based on monomer, glass, or metal infusion of a fired suspension, i.e., a ceramic network, or monomer infusion of a partially, glass infused ceramic network may present advantages over currently available restorations, such as composite resin and ceramic restorations, with respect to wear resistance and strength. It is a technical advantage that such a restorative material may have improved wear resistance and flexibility with respect to conventional composite resins and ceramics. It is a further technical advantage that in restorative materials made according to this invention, the masticatory surface, e.g., the coronal portion, may be glass infused to provide a hard, wear resistant restoration. For example, a glass layer may have a hardness in a range of about 300 to 600 KHN and an elastic modulus in a range of about 15 to 25×10$^6$ PSI. In addition, it may have a flexural strength of about 240 MPa, and the monomer infused interior may have a flexural strength of about 80 MPa. For example, an inlay, onlay, crown, or bridge fabricated from monomer infused restorative material produced according to this invention may be affixed to a natural tooth or metal restoration supporting structure(s) with resin cements. Further, a restoration fabricated from a metal alloy infused restorative material may be hard, but also flexible and easily machined.

It is a technical advantage that the invention produces an odontoform in which a glass layer with a thickness of about 1.5 mm, e.g., about 1 to 2 mm, may be formed in the coronal portion, which is similar to natural tooth enamel. It is another technical advantage that because the depth of the infused glass layer in the coronal portion approximates the depth of natural enamel, the preparation of a restoration in the odontoform closely resembles the preparation of such a restoration in natural teeth. In addition, for examination purposes, such odontoforms provides a more realistic subject for the preparation and evaluation of restorations than present odontoforms, such as plastic teeth. It is also a technical advantage that caries present in natural teeth may be simulated on odontoforms of the invention by etching or machining the glass infused coronal portion. This adds an additional degree of realism to the odontoform.

Other objects, advantages, and features will be apparent when the detailed description of the invention and the drawings are considered.

BRIEF DESCRIPTION OF THE DRAWINGS

For a more complete understanding of the present invention and the technical advantages thereof, reference is made to the following description taken in conjunction with accompanying drawings, in which.

DETAILED DESCRIPTION OF THE INVENTION

Figure 2:
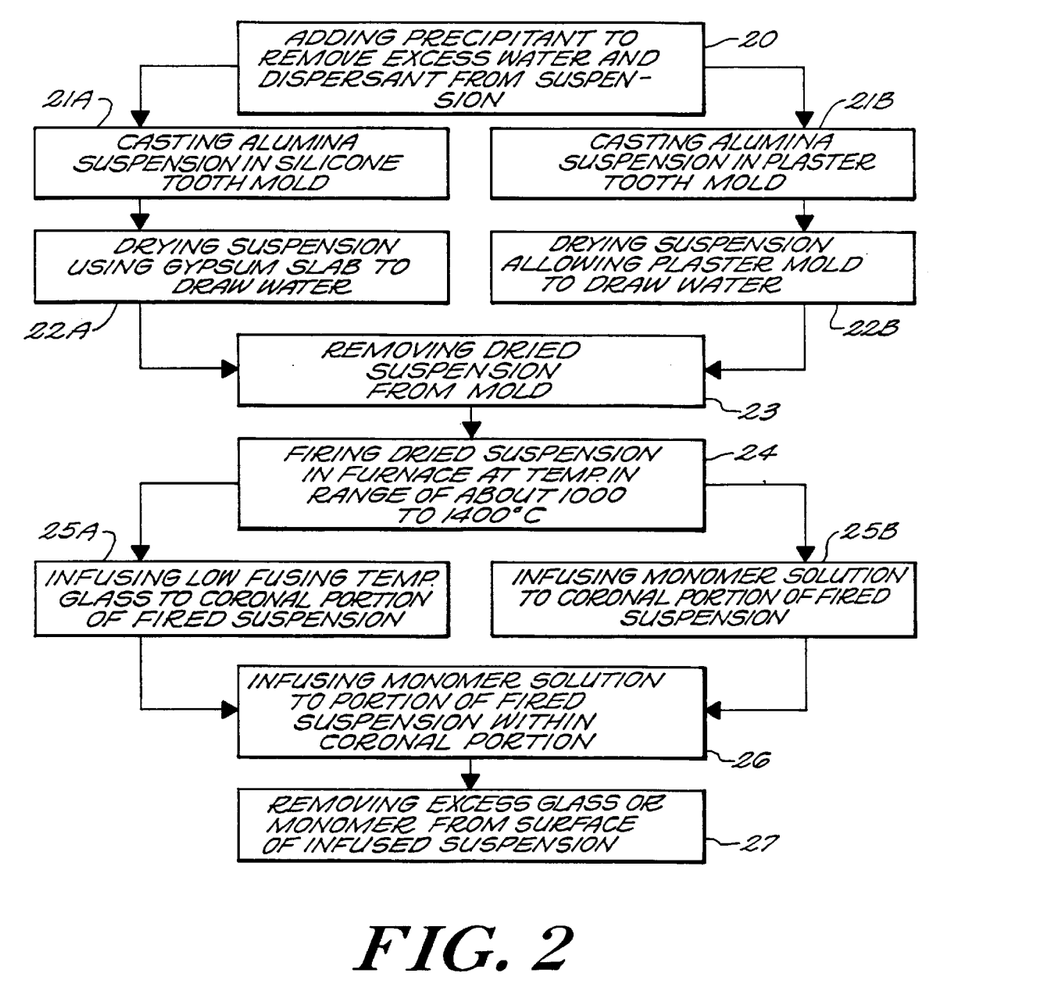
FIG. 2 is a flow chart depicting the steps of an embodiment of a process of this invention.

In a first embodiment, the invention involves the creation of an interpenetrating network material of ceramic, glass, and monomer with improved resistance to wear. Referring to FIG. 2, an embodiment of the process includes the colloidal casting of a suspension of ceramic particles in a mold. This process is based on colloidal processing of materials. Colloidal processing involves the intimate mixing of two substances, one of which may be referred to as the dispersion phase or colloid, e.g., the ceramic particles, and is uniformly distributed in a finely divided state throughout a second substance. The second substance may be refereed to as the dispersion or dispersing medium e.g., deionized water. The dispersion medium may be a solid, liquid, or gas, and the mixture of the substances is known as a colloidal suspension.

The ceramic particles in the suspension may be metal oxides, such as alumina and zirconia, or feldspathic glasses, such as sodium and potassium feldspar and nepheline glasses, or the like. The mechanical properties, as well as the color, of the suspension may be altered by the choice of ceramic particles. An alumina suspension may be created in deionized water with a pH in the range of about 2 to 6, e.g., about 4 to 5. An acid, such as nitric or citric acid, may be added to the deionized water to lower pH.

A dispersant is added to the deionized water to promote a substantially uniform dispersion of the ceramic particles throughout the suspension. Suitable dispersants include acids, such as benzoic acids and acrylic acids; alcohols, such as polyvinyl alcohol; organic polymers, such as polyvinyl pryollidone and cellulose, including cellulose esters; silicates, such as sodium silicate; and derivatives of these. Benzoic acids further may include p-hydroxy and p-amino benzoic acid, and acrylic acids may include methacrylic acids. If the dispersant is a polyvinyl alcohol, it may be in solution with water at a concentration of about 0.5 to 2% by weight. The suspension is mixed, e.g., sonicated, to further promote dispersion of the ceramic particles. For example, an ultrasonicator, such as the Heat Systems Ultrasonicator, may be used, and the suspension may be sonicated at a 25% power level for a period of between about 5 and 20 minutes.

In step 20 of FIG. 2, a precipitant may be added to the suspension to remove excess water and dispersant before casting. For example, if the dispersant is polyvinyl alcohol, a non-solvent, such as acetone, may be added to precipitate a more concentrated ceramic suspension. Alternatively, a precipitant may be added to the suspension after casting. Regardless, when the precipitant is added to the suspension, the precipitate is a coacervate, i.e., an aggregate of colloidal droplets bound together by the force of electrostatic attraction.

The alumina suspension (colloidal) may be cast in a rubber mold of a tooth as described in step 21A. The rubber mold may be made from silicone, polysulfide, or polyether-based rubbers. Rubber molds are desirable because they are easily deformed to remove the dried suspension. The base of such a tooth mold may be exposed, and a slab of a calcium sulfate hemihydrate based material, e.g., a gypsum slab, may be set on the mold in contact with the suspension. According to step 22A, the calcium sulfate material draws water from and dries the suspension, thereby, solidifying the alumina mass. Preferably, the suspension is allowed to dry in this manner for about 24 hours before being removed from the mold.

Alternatively, the suspension may be cast in a plaster mold, i.e., slip cast, as described in step 21B. A calcium sulfate hemihydrate based material, such as gypsum, is a common ingredient in plaster for use in fabricating such molds, and water is drawn from the suspension into the plaster, according to step 22B. It may be necessary to break such plaster molds in order to remove the dried suspension. Nevertheless, such molds are inexpensively and easily fabricated, and the plaster may be reusable or disposable.

After the dried suspension is removed from the mold, as indicated in step 23, the dried alumina suspension is fired in a furnace at a temperature in a range of about 1000° to 1400° C., according to step 24. In order to avoid thermal shock, the dried suspension may be placed in a cold furnace and heated gradually to the firing temperature. For example, the temperature of the furnace may be raised at a rate of about 2° to 15° C. per minute until the desired firing temperature is reached.

Referring to step 25A, the coronal portion of the fired suspension is then infused with a glass, such as lanthanum aluminosilicate glass or borosilicate glass, or a combination thereof, for about 0.5 to 1 hours at about 1100° C. This achieves a glass layer depth of about 1 to 2 mm. Alternatively, as indicated in step 25B, the coronal portion of the fired suspension may be infused with a monomer, such as a light or heatcured monomer. Such monomers, e.g., a mixture of triethylene glycol dimethacrylate (TEGDMA) and 2,2bis[4(2-hydroxy-3methacryloyloxy-propyloxy)-phenyl]propane (BISGMA), may have a hardness in a range of about 40 to at least about 60 KHN and a flexural strength in a range of about 50 to 80 MPa. For example, a heat-cured monomer may be cured in a low heat furnace at a temperature in a range of about 40° to 75° C. for about 24 hours. Moreover, camphoroquinone and benzoyl peroxide may be added to the monomer to effect light curing. Such a light-cured monomer may be cured with light in the visible blue spectrum for about 15 minutes.

Suitable monomers include acrylic monomers, such as hydroxy ethyl methacrylate (HEMA), TEGDMA, and BIS-GMA. Other suitable monomers include urethane dimethacrylate (UDM), biphenyldimethacrylate (BPDM), n-tolyglycineglycidylmethacrylate (NTGE), and polyethylene glycol dimethacrylate (PEG-DMA). Such monomers may be used alone, or two or more monomers may be used in combination. Further, colloidal silica may be added to the monomer to alter its index of refraction. By altering the monomer's index of refraction, the color of the odontoform or restoration may be adjusted. Moreover, acetone may be added to individual monomers (or monomer solutions) to alter their viscosity and control the rate of infusion.

The ceramic network also may be infused with a metal alloy to form a metal alloy layer. A suitable metal alloy has a melting point at least about 50° C. less than the ceramic network. For example, if the ceramic network includes alumina, a metal alloy including at least about 60% by weight of gold and at least about 5 to 10% by weight palladium or platinum, or both. Such a gold infused ceramic may be highly ductile, and appropriate adjustment of the ceramic network may produce a metal-ceramic material which retains many of the properties of the infused metal. These properties may include increased flexion and burnish ability and resistance to fracture.

As described in step 26, the fired suspension, at least the portion within the layer of glass or monomer (or a metal alloy), may be infused with a light or heat-cured monomer, or both. As discussed above, the monomer used for the infusion may be selected to change the mechanical properties of the portion to which it is infused. Moreover, the type of monomer may be varied, so that the coronal portion is hard, e.g., to a hardness of about 40 to at least about 60 KHN, and the internal portion is softer. Alternatively, if the fired suspension is to be used as part of a dental restoration, the entire fired suspension may be infused with either monomer or metal alloy.

Excess glass, monomer, or metal alloy may be removed from the surface of the infused suspension, by using, for example, air abrasion or grinding, as described in step 27. If air abrasion is used to remove the excess glass or monomer from a fired suspension which contains alumina particles, alumina particles with a mean diameter of about 50 $\mu$m are preferred as the abrasive. Such alumina particles are preferred as the abrasive because they minimize the contamination of the fired and infused suspension.

Figure 3:
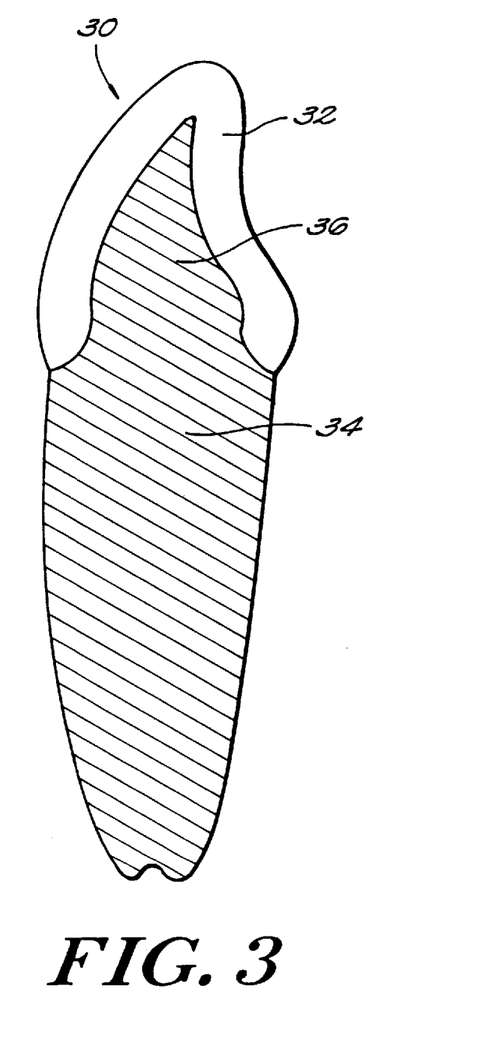
FIG. 3 is a cross-sectional view of an odontoform manufactured by a process of the present invention.

Referring to FIG. 3, a cross-sectional view of an odontoform 30 manufactured according to a process of the invention is shown. Odontoform 30 is cast in a tooth-shaped mold (not shown). As discussed above, the mold may be a rubber, e.g., silicone; a plaster; or a split-metal mold. A glass layer 32 is infused in a coronal portion of odontoform 30, which corresponds to the portion of a natural tooth which is exposed above healthy gingiva and extends to a depth of about 1 to 2 mm below the surface of the tooth crown 31. Suitable glasses may include lanthanum aluminosilicate glass, borosilicate glass, or a combination of these glasses, or other low fusing temperature glasses. Glass layer 32 has a depth of about 1 to 2 mm and may be infused uniformly over the coronal portion of odontoform 30. Alternatively, as discussed above, a monomer may be infused to the coronal portion of odontoform 30. Such a monomer is selected to achieve an increased hardness in the coronal portion, but less than that obtained in glass layer 32.

In addition, at least a first portion 34 of odontoform 30, including a second portion 36 within glass layer 32, may be infused with a monomer, such that first portion 34 has physical and mechanical properties that are different from those of glass layer 32 and that generally are similar to those of natural dentin. For example, the glass layer may have a hardness in a range of about 300 to 600 KHN, an elastic modulus in a range of about 15 to $25 \times 10^6$ PSI. In addition, the glass layer may have a flexural strength of about 240 MPa. Further, a pulp cavity (not shown) may be hollowed out in first and second portions 34 and 36. For example, the pulp cavity may be filled with a gel, an acrylic, or another material chosen because of its similarity to the physical and mechanical properties and color of pulp. In addition, caries found in natural teeth may be simulated on such an odontoform by acid etching or machining of the glass or monomer or metal alloy layer.

In a second embodiment, this invention involves a process for making a suspension infused with a monomer to produce a material which is suitable for use in the fabrication of dental restorations, such as dental onlays, inlays, crowns, and bridges. A suitable restorative material has a structure with mechanical properties, such as an elastic modulus, similar to those of dentin in natural teeth. Presently, acrylic and metal are used as supporting structures for restorations and for testing restorations, such as ceramic crowns. However, the mechanical properties of these materials are much different from those of natural dentin and, thus, may give inferior results.

Figure 4:
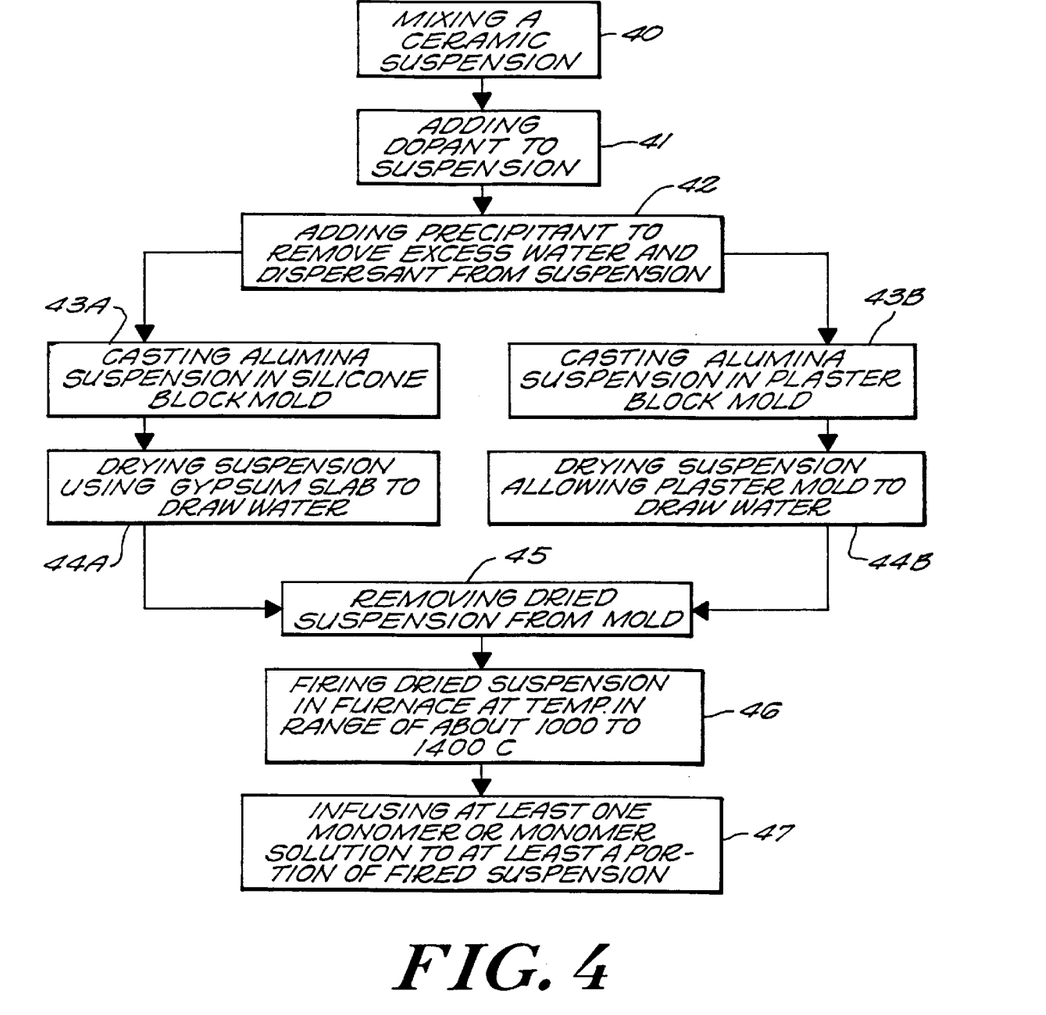
FIG. 4 is a flow chart depicting the steps of another embodiment of a process of this invention.

This second embodiment also involves the colloidal processing of ceramic particles. The ceramic particles again may include metal oxides and feldspathic glasses. The particles may have an average particle size of about 0.1 to 10 mm. Referring to FIG. 4, colloidal processing of the material may be accomplished by using ceramic particles to create a suspension. See step 40. If the ceramic particles are metal oxides, such as alumina or zirconia, dopants in concentrations of about 0.15 to 5% by weight may be mixed with the ceramic particles in order to alter, i.e., increase or decrease, the sintering temperature and control grain growth and densification of the ceramic suspension, as described in step 41. The dopants effect the mass transport of the metal oxides. The sintering temperature, grain growth, densification vary with the dopant selected and its quantity. These dopants may be selected from the group consisting of CaO, $SiO_2$, $TiO_2$, $Fe_2O_3$, $Cr_2O_3$, MgO, ZnO, $Li_2O$, $Na_2O$, $K_2O$, and PbO. Further, the suspension of step 40 may contain a single type of ceramic particles or a combination of several types of ceramic particles.

In a suitable suspension, about 100 grams of ceramic particles are added to about 150 ml of deionized water and mixed, e.g., sonicated, with an ultrasonicator. If a Heat Systems Ultrasonicator is used, the suspension may be sonicated for about 10 minutes at about 25% power. About 150 ml of a solution containing about 0.1 to 2% by weight of polyvinyl alcohol may be added to the ceramic suspension. The pH of the suspension then may be adjusted to make the suspension acidic or basic. If acidic, the pH may be lowered to a range of about 2 to 6, e.g., about 4 to 5. An acid, such as nitric or citric acid, may be added to the deionized water to lower pH. If basic, the pH may be raised to about 8 to 11, e.g., about 9 to 10. A hydroxide, such as sodium hydroxide, may be added to the deionized water to raise pH.

After adjustment of the pH, the suspension may again be ultrasonicated. If the Heat Systems Ultrasonicator is used, the suspension may be sonicated for about 15 minutes at about 25% power. After mixing of the suspension is complete, a concentrated ceramic suspension may be brought out, i.e., precipitated, using a non-solvent, such as acetone or citric acid, as described in step 42. These non-solvents render polyvinyl alcohol insoluble in water.

The suspension (or the coacervate) then may be centrifugally cast or pressure cast in a rubber, plaster, or split-metal mold. Centrifugal casting may be performed at about 3000 rpm for between about 0.25 to 2 hours. Alternatively, pressure molding or filtration casting also may be used. In pressure molding, the mold is placed in a die, and the suspension is then placed on top of the die. Pressure is then applied to the suspension, e.g., by means of a piston or by compressed air, to drive the suspension into the mold. Pressure applied may range from about 500 to 25,000 PSI.

Referring again to FIG. 4, the suspension may be cast in a rubber mold, as indicated in step 43A. The base of the mold may be open to expose the suspension, and a slab of a calcium sulfate hemihydrate based material, e.g., a gypsum slab, may be placed in direct contact with the suspension. According to step 44A, such a calcium sulfate material draws water from the suspension. Alternatively, the suspension may be cast in a plaster mold, e.g., slip cast, according to step 43B. The suspension is allowed to dry before being removed from the mold and placed in the furnace to burn off remaining dispersant. See Step 44B. For example, in order to burn off polyvinyl alcohol, the suspension may be heated to about 600° C.

The dried suspension is removed from the mold and is placed in a furnace and fired, e.g., sintered, such that shrinkage is less than about 1%. See Steps 45 and 46. Firing temperatures may vary according to the specific ceramic particles included in the suspension. In the case of feldspathic glass, for example, the firing temperature may be in a range of about 600° to 1200° C. When the ceramic particles are metal oxides, however, this temperature may be in a range of about 1000° to 1400° C. As discussed above, in order to avoid thermal shock, the dried suspension may be placed in a cold furnace and heated gradually to the firing temperature. For example, the temperature of the furnace may be raised at a rate of about 2° to 15° C. per minute until the desired firing temperature is reached.

Referring to step 47, after firing, the suspension, i.e., the ceramic network, is infused with a coating agent, such as silane, and a monomer with an index of refraction close to that of the ceramic in order to produce a translucent material. Suitable monomers may consist of a light-cured or heat-cured monomer, or both. For example, as discussed above, a heat-cured monomers may be cured in a low heat furnace at about 40° to 75° C. for about 24 hours while a light-cured monomer may be cured with light in the visible blue spectrum for about 15 minutes.

Again, suitable monomers include acrylic monomers, such as HEMA, TEGDMA, and BIS-GMA. Other suitable monomers include UDM, BPDM, NTGE, and PEG-DMA. Again, these monomers may be used alone, or two or more monomers may be used in combination Further, as discussed above, colloidal silica may be added to the monomer to alter its index of refraction. By altering the monomer's index of refraction, the color of the restoration or restorative material may be adjusted. Infusion with such monomers may take between about 1 and 24 hours depending upon their viscosity. Acetone may be added to individual monomers (or monomer solutions) to alter their viscosity and, thereby, control the rate of infusion.

This invention may be further clarified by a consideration of the following examples which are intended to be purely exemplary of the use of the invention. A ceramic suspension was prepared including feldspathic glass ceramic particles dispersed in a medium containing deionized water and a concentration of polyvinyl alcohol in a range of about 0.5 to 2% by weight. The suspension was filtration cast in brass molds to form discs, and the molded suspension discs were dried. Moreover, the discs were heated to at least about 600° C. to burn off the polyvinyl alcohol.

Discs of the dried suspension then were fired, e.g., sintered, at 1000° C., 1050° C., and 1100° C. to form a ceramic network and to produce minimum shrinkage and variations in the ceramic network. After firing, the discs were placed in glass discs containing sufficient amounts of a monomer solution including TEGDMA, BIS-GMA, and HEMA to infuse the ceramic network. The monomer infused discs were then heat and light cured, as described above. Bars measuring 1.5 mm×2.0mm×2.5mm were machined from the discs and were polished with diamond past having a mean particle size of 15 $\mu$m. The flexural strength of the bars was determined as follows:

| Firing Temperature | Flexural Strength |
|---|---|
| 1000° C. | 25.34 ± 3.68 MPa |
| 1050° C. | 81.25 ± 11.96 MPa |
| 1100° C. | 90.15 ± 13.65 MPa. |

A fourth disc was fired at 1050° C. and infused with a silane coating agent before infusion with the monomer solution. The flexural strength of a bar machined from this disc was determined to be 117.70±15.07 MPa. With the exception of the silane infused ceramic network, each network had a lower flexural strength than an infused ceramic.

Conventional dental composite resins produce a restorative material with only about 60 volume % of ceramic filler. The process of the invention, however, may produce a restorative material within a range of about 65–90 volume % of ceramic filler. A restoration formed on a metal supporting structure may be used without further modification, except for minor adjustments to the biting surface and internal surface too improve occlusion. Thus, the process may be used to fabricate dental restorations directly. When the suspension has been molded, e.g., pressure molded, into blocks, however, ceramic machining systems may be used to produce onlays, inlays, crowns, and bridges. Blocks of the fired and infused suspension may be used to manufacture implants for dentistry and medicine. Dental implants for tooth replacement and medical implants for bone or joint replacement may be fabricated from blocks of a monomer (or metal alloy or glass) infused suspension. Such materials are particularly useful in Computer Aided Design-Computer Aided Machining (CAD-CAM) systems, as well as copy milling systems, such as Mikrona Corporation's CELAY® copy milling system.

A process of this invention may produce restorative materials by the infusion of a dried ceramic suspension with a monomer, glass, or metal alloy. Traditional composite materials possess discreet and isolated phases dispersed in a network. A material having interpenetrating network involves the intertwining of two different types of materials. This intertwined network produces a single material with improved mechanical properties. This material may be produced by filling the pores of an open pore network of one material with a second material. When the pores of the first material are continuous throughout, capillary action may be used to draw the second material into the pores to create an interpenetrating network.

The infused suspension produces an improved restorative material which resists pull out of the filler because the ceramic particles are connected to each other and intertwined with monomer (or metal alloy or glass). Wear may be reduced due to the high filler content, as well as the interpenetrating network of the monomer and ceramic filler.

The material also may withstand flexing forces better than all-ceramic restorations because of the flexibility of the monomer (or metal alloy).

Other embodiments of the invention will be apparent to the skilled in the art from a consideration of this specification or practice of the invention disclosed herein. Although a detailed description and examples of the present invention has been provided above, it is to be understood these are exemplary and that the scope of the invention is not be limited thereby, but is to be determined by the claims which follow.

I claim:

1. A process for producing a ceramic network material form a ceramic suspension, wherein said suspension includes dispersed ceramic particles in a medium containing water and a dispersant, comprising the steps of:

casting said suspension in a mold;

drying said molded suspension to draw said water from said suspension;

firing said dried suspension to form a ceramic, open pore network;

infusing at least a portion of said ceramic network with a silane coating agent; and infusing a monomer to at least a portion of said ceramic network.

2. The process of claim 1, wherein said monomer is an acrylic monomer.

3. The process of claim 1, wherein said monomer comprises at least one monomer selected from the group of acrylic monomers consisting of hydroxy ethyl methacrylate (HEMA), triethylene glycol dimethacrylate (TEGDMA), 2,2-bis[4(2-hydroxy-3 Methacryloyloxy-propyloxy)-phenyl] propane (BIS-GMA), urethane dimethacrylate (UDM), biphenyldimethacrylate (BPDM), n-tolyglycine-glycidylmethacrylate (NTGE), and polyethylene glycol dimethacrylate (PEG-DMA).

4. The process of claim 1, wherein said monomer is selected from the group consisting of heat-cured monomers and light-cured monomers.

5. The process of claim 1, wherein said mold is tooth-shaped and the process further comprises the step of infusing a low fusing temperature glass to a coronal portion of said ceramic network to form a glass layer within said ceramic network with a thickness in a range of about 1 to 2 mm; and wherein said infused portion is within said glass layer.

6. The process of claim 5, wherein said low fusing temperature glass is selected from the group consisting of lanthanum aluminosilicate glass and borosilicate glass.

7. The process of claim 5 wherein the step of infusing the low fusing temperature glass includes heating said ceramic network and said low fusing temperature glass for a period of about 0.5 to 1 hours at about 1100° C.

8. The process of claim 5, further comprising the step of removing low fusing temperature glass on a surface of said ceramic network.

9. The process of claim 8, wherein said glass is removed by a method selected from the group consisting of air abrading and grinding.

10. The process of claim 5, further comprising the step of etching said glass layer to give the appearance of caries.

11. The process of claim 1, further wherein said water is acidic and has a pH in a range of about 2 to 6.

12. The process of claim 1, further wherein said water is basic and has a pH in a range of about 8 to 11.

13. The process of claim 1, wherein said mold is a plaster mold, such that when said suspension is cast in said mold, said water is drawn from said suspension in said plaster mold, thereby drying said suspension.

14. The process of claim 1, wherein said dispersed ceramic particles are selected from the group consisting of metal oxides and feldspathic glasses.

15. The process of claim 1, wherein said suspension is fired in a furnace at a temperature in a range of about 600° to 1400° C.

16. The process of claim 1, wherein said dispersed ceramic particles are metal oxides and said suspension is fired in a furnace at a temperature in a range of about 1000° to 1400° C.

17. The process of claim 1, wherein said dispersed ceramic particles are feldspathic glasses and said suspension is fired in a furnace at a temperature in a range of about 600° to 1200° C.

18. The process of claim 1, wherein said dispersant is selected from the group consisting of acids, alcohols, organic polymers, silicates, and derivatives.

19. The process of claim 1, wherein said ceramic particles are metal oxides, further comprising adding a dopant to said ceramic particles, wherein said dopant selected from the group consisting of $CaO$, $SiO_2$, $TiO_2$, $Fe_2O_3$, $Cr_2O_3$, $MgO$, $ZnO$, $Li_2O$, $Na_2O$, $K_2O$, and $PbO$.

20. The process of claim 19, wherein said dopant is added to said dispersion in a concentration of about 0.15 to 5% by weight.

21. The process of claim 1, further comprising the step of adding a precipitant to said suspension to remove excess water and dispersant from said suspension.

22. The process of claim 21, wherein said precipitant is selected from the group consisting of acetone and citric acid.

23. The process of claim 1, further comprising the step of curing said monomer.

24. The process of claim 1, wherein said step of infusing further comprises using capillary action to draw said monomer into said network.

25. The process of claim 1, wherein said network has pores that are continuous throughout said network.

26. A process for producing a ceramic network material from a ceramic suspension, wherein said suspension includes dispersed ceramic particles in a medium containing water and a dispersant, comprising the steps of:

casting said suspension in a mold;

drying said molded suspension to draw said water from said suspension;

firing said dried suspension to form a ceramic network; and infusing a monomer to at least a portion of said ceramic network, wherein said mold is made from rubber and when said suspension is cast in said mold, a base of said mold is exposed, such that the step of drying said suspension comprises placing a slab of calcium sulfate in contact with said base, thereby drawing said water from said suspension in said slab.

27. A process for producing a ceramic network material from a ceramic suspension by casting said suspension in a tooth-shaped mold, wherein said suspension includes alumina particles dispersed in a medium containing deionized water with a pH in a range of about 4 to 5 and a concentration of polyvinyl alcohol in a range of about 0.5 to 2% by weight, comprising the steps of:

casting said suspension in said mold;

drying said molded suspension to draw said water from said suspension;

firing said dried suspension in a furnace at a temperature in a range of about 1000° to 1200° C. to form a ceramic network;

infusing lanthanum aluminosilicate glass to a coronal portion of said ceramic network to form a glass layer within said fired suspension with a thickness in a range of about 1 to 2 mm; and infusing a monomer to at least a portion of said ceramic network within said glass layer.

28. The process of claim 27, further comprising the step of curing said monomer.

29. A process for producing a ceramic network material from a ceramic suspension by casting said suspension in an mold, wherein said suspension includes dispersed ceramic particles having diameters in a range of about 0.1 to 10 $\mu$m in a medium containing deionized water with a pH selected from the group of ranges consisting of about 2 to 6 and about 8 to 11 and a concentration of polyvinyl alcohol in a range of about 0.1 to 2% by weight, comprising the steps of:

casting said suspension in said mold;

drying said molded suspension in a furnace at a temperature in a range of about 600° to 1400° C. to form a ceramic, open pore network;

infusing at least a portion of said ceramic network with a silane coating agent; and infusing a monomer to at least a portion of said ceramic network.

30. The process of claim 29, wherein said monomer is an acrylic monomers.

31. The process of claim 29, wherein said ceramic particles are metal oxides, further comprising adding a dopant to said ceramic particles, wherein said dopant selected from the group consisting of CaO, $SiO_2$, $TiO_2$, $Fe_2O_3$, $Cr_2O_3$, MgO, ZnO, $Li_2O$, $Na_2O$, $K_2O$, and PbO.

32. The process of claim 31, wherein said dopant is added to said dispersion in a concentration of about 0.15 to 5% by weight.

33. The process of claim 29, further comprising the step of adding a precipitant to said suspension to remove excess water and dispersant from said suspension.

34. The process of claim 33, wherein said precipitant is selected from the group consisting of acetone and citric acid.

35. The process of claim 29, further comprising the step of curing said monomer.

36. A process for producing a ceramic network material from a ceramic suspension, wherein said suspension includes dispersed ceramic particles in a medium containing water and a dispersant, comprising the steps of:

casting said suspension in a mold;

drying said molded suspension to draw said water from said suspension;

firing said dried suspension to form a ceramic, open pore network;

infusing at least a portion of said ceramic network with a silane coating agent; and infusing a monomer to at least a portion of said ceramic network.

37. The process of claim 36, wherein said step of infusing further comprises using capillary action to draw said material into said network.

38. The process of claim 36, wherein said network has pores that are continuous throughout said network.

* * * * *